(12) United States Patent
Deev et al.

(10) Patent No.: US 11,406,739 B2
(45) Date of Patent: Aug. 9, 2022

(54) METHOD FOR CREATING A PERSONALIZED GENE-ACTIVATED IMPLANT FOR REGENERATING BONE TISSUE

(71) Applicant: "NEXTGEN" COMPANY LIMITED, Moscow (RU)

(72) Inventors: Roman Vadimovich Deev, St. Petersburg (RU); Artur Aleksandrovich Isaev, Moscow (RU); Ilya Yadigerovich Bozo, Kuvshinovo (RU); Vladimir Sergeevich Komlev, Moscow (RU); Alexey Yurevich Drobyshev, Moscow (RU)

(73) Assignee: "NEXTGEN" COMPANY LIMITED, Moscow (RU)

( * ) Notice: Subject to any disclaimer, the term of this patent is extended or adjusted under 35 U.S.C. 154(b) by 0 days.

(21) Appl. No.: 15/480,698

(22) Filed: Apr. 6, 2017

(65) Prior Publication Data

US 2017/0209626 A1 Jul. 27, 2017

Related U.S. Application Data

(63) Continuation of application No. PCT/RU2015/000667, filed on Oct. 13, 2015.

(30) Foreign Application Priority Data

Feb. 10, 2015 (RU) .......................... RU2015104291

(51) Int. Cl.
| | |
|---|---|
| *A61L 27/58* | (2006.01) |
| *A61F 2/28* | (2006.01) |
| *A61L 27/54* | (2006.01) |
| *A61K 31/7088* | (2006.01) |
| *A61K 48/00* | (2006.01) |
| *C12N 15/87* | (2006.01) |
| *A61K 47/50* | (2017.01) |
| *A61L 27/14* | (2006.01) |
| *A61L 27/36* | (2006.01) |
| *B33Y 70/00* | (2020.01) |
| *B33Y 80/00* | (2015.01) |

(52) U.S. Cl.
CPC ............... *A61L 27/58* (2013.01); *A61F 2/28* (2013.01); *A61K 31/7088* (2013.01); *A61K 47/50* (2017.08); *A61K 48/00* (2013.01); *A61L 27/14* (2013.01); *A61L 27/3641* (2013.01); *A61L 27/54* (2013.01); *C12N 15/87* (2013.01); *A61L 2430/02* (2013.01); *B33Y 70/00* (2014.12); *B33Y 80/00* (2014.12)

(58) Field of Classification Search
CPC ...... A61L 27/58; A61L 27/14; A61L 27/3641; A61L 27/54; A61L 2430/02; A61L 27/3834; A61K 31/7088; A61K 48/00; A61K 47/50; C12N 15/87; A61F 2/28; B33Y 70/00; B33Y 80/00; A61P 19/00

See application file for complete search history.

(56) References Cited

U.S. PATENT DOCUMENTS

| | | | |
|---|---|---|---|
| 5,962,427 A | 10/1999 | Goldstein et al. | |
| 7,427,602 B1 * | 9/2008 | Shea | A61K 9/1647 424/422 |
| 2012/0282573 A1 * | 11/2012 | Mao | A61L 27/46 433/202.1 |
| 2014/0011162 A1 | 1/2014 | Zegarelli | |
| 2015/0283298 A1 * | 10/2015 | Kaplan | A61L 27/12 424/93.7 |

FOREIGN PATENT DOCUMENTS

| | | | |
|---|---|---|---|
| RU | 2170104 | 7/2001 | |
| WO | WO-2013100818 A2 * | 7/2013 | ............. A61K 35/12 |

OTHER PUBLICATIONS

Sun et al. "Zero Echo Time Magnetic Resonance Imaging of Contrast-Agent-Enhanced Calcium Phosphate Bone Defect Fillers." Tissue Eng Part C Methods. Apr. 2013; 19(4): 281-287. (Year: 2013).*
Rerko et al. "Comparison of various imaging techniques to quantify glenoid bone loss in shoulder instability." J Shoulder Elbow Surg. Apr. 2013;22(4):528-34. (Year: 2013).*
Deev et al. "Efficiency of gene-activated osteoplastic material with plasmid DNA containing VEGF gene for bone defects healing" Cellular Transplantation and Tissue Engineering, 2013; VIII (3): 78-85 (Year: 2013).*
Henkel et al. "Repair of bone defects by applying biomatrices with and without autologous osteoblasts." J Craniomaxillofac Surg. Feb. 2005;33(1):45-9. (Year: 2005).*
Durna et al. "Research and Development of Laser Engraving and Material Cutting Machine from 3D Printer." Management Systems in Production Engineering 28.1 (2020): 47-52. (Year: 2020).*
International Search Report dated Dec. 24, 2015, in International application No. PCT/RU2015/000667 (w/ English translation).
Al-Nawas et al, "Augmentation procedures using bone substitute materials or autogenous bone—a systematic review and meta-anaiysis", *Eur. J. Oral Implantol.*, 2014, vol. 7 (Suppl), pp. S1-S16.
Amini et al, "Bone tissue engineering: recent advances and challenges", *Crit Rev Biomed Eng.*, 2012, vol. 40, No. 5, pp. 363-408.

(Continued)

*Primary Examiner* — Titilayo Moloye
(74) *Attorney, Agent, or Firm* — Oblon, McClelland, Maier & Neustadt, L.L.P.

(57) ABSTRACT

Provided is a method for construction of bone substitutes efficient in the repair of large bone defects. The method for constructing such medical products includes three-dimensional printing of a bioresorbable scaffold and its activation by gene constructions. Produced medicinal products may serve as an efficient alternative to bone autografts.

19 Claims, 4 Drawing Sheets
(3 of 4 Drawing Sheet(s) Filed in Color)

(56) References Cited

OTHER PUBLICATIONS

Bozo et al,, "Local gene therapy in bone reconstruction", Materialy 1-go Natsionalnogo Kongressa po regenerativnoi meditsine M., "MEDI Ekspo", Dec. 4-6, 2013 goda, p. 30, Found on the internet: URL: http://www.mediexpo.ru/fileadmin/user_upload/content/pdf/thesis/thesis_nkrm13.pdf p. 30 (w/English translation).

Bronstein D.A. et al, "Clinical parameters of osteo- and soft tissue integration of dental implants for various methods of overdenture retention" Materialy 1-go Natsionalnogo Kongressa po regenerativnoi meditsine M., "MEDI Ekspo", Dec. 4-6, 2013 goda, p. 37. Found on the internet: URL: http://www.mediexpo.ru/fileadmin/user_upload/content/pdf/thesis/thesis_nkrm13.pdf p. 37 (w/English translation).

Deev et al, "Construction and biological effect evaluation of gene-activated osteoplastic material with human VEGF gene", *Cellular Transplantation and Tissue Engineering*, 2013, vol. VIII, No. 3, pp. 78-85 (w/English abstract).

Han et al, "Single versus dual venous anastomoses of the free fibula osteocutaneious flap in mandibular reconstruction: a retrospective study", *Microsurgery*, 2013, vol. 33, pp. 652-655.

Higashino et al, Single venous anastomosis versus dual venous anastomoses in free anterolateral thigh flap transfer: A cohort study, *Journal of Plastic, Reconstructive & Aesthetic Surgery*, (2016), http://dx.doi.org/10/1016/j.bjps.2016.06.023.

Nkenke et al, "Autogenous bone harvesting and grafting in advanced jaw resorption: Morbidity, resorption and implant survival", *Eur J Implantol*, 2014; vol. 7 (Suppl2): pp. S203-S217.

Pipitone et al, "Management of traumatic bone loss in the lower extremity", *Orthop. Clin. North. Am.*, 2014, vol. 45, No. 4, pp. 469-482.

Strobel et al, "Induction of bone formation in biphasic calcium phosphate scaffolds by bone morphogenetic protein-2 and primary osteoblasts", *J Tissue Eng Regen Med*, 2012, vol. 8, No. 3, pp. 176-185.

Tevlin et al, "Biomaterials for craniofacial bone engineering", *J Dent Res*, 2014, vol. 93, No. 12, pp. 1187-1195.

Wegman et al, "Osteogenic differentiation as a result of BMP-2 plasmid DNA based gene therapy in vitro and in vivo", *Eur Cells & Mater*, 2011, vol. 21, pp. 230-242.

International Preliminary Report on Patentability dated Aug. 24, 2017, in International application No. PCT/RU2015/000667.

* cited by examiner

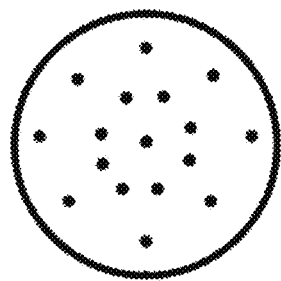 
FIG. 1A  FIG. 1B
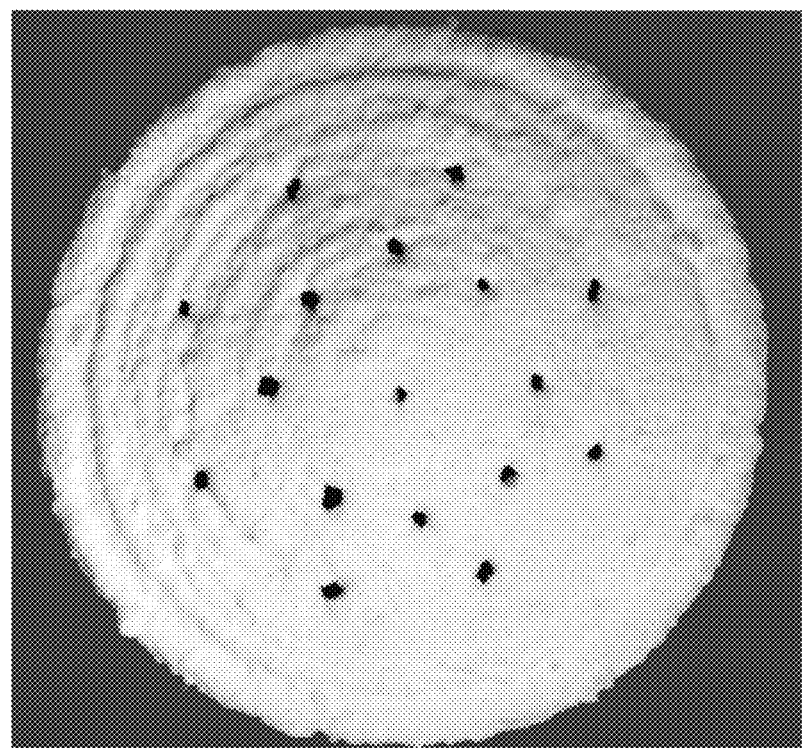
FIG. 2

METHOD FOR CREATING A PERSONALIZED GENE-ACTIVATED IMPLANT FOR REGENERATING BONE TISSUE

CROSS-REFERENCE TO RELATED APPLICATIONS

This application is a continuation of and claims priority to Application PCT/RU2015/000667, filed Oct. 13, 2015, that claims priority to Russian Patent Application RU 2015104291, filed Feb. 10, 2015, the contents of which are hereby incorporated herein by reference in their entirety.

BACKGROUND

Field of the Disclosure

The present disclosure pertains to construction of a personalized matrix of biocompatible and bioresorbable materials and their combination with a biologically active component such as gene constructions.

Discussion of the Background

A problem of treating patients with bone defects or bone atrophy is highly pressing in the practice of traumatology and orthopedics, maxillofacial and oral surgery [1-3]. A variety of bone substitutes (osteoplastic materials) exist for healing small bone defects, and there are methods to optimize the materials by mixing, e.g., with an autogenous bone tissue, platelet-rich plasma, and/or plasma rich in growth factors. [1].

However, particularly pressing and socially important is the unsolved problem of efficient treatment of patients with large bone defects (over 1 cm$^3$) associated with congenital deformities and abnormal development, traumas, inflammatory diseases, oncologic pathology and first stages of surgical treatment thereof. In these clinical situations where the bone function as a body organ is impaired to a considerable extent or is completely lost, it is impossible to reconstruct the bone continuity using commercially available bone substitutes given the pronounced osteogenic insufficiency. Only autogenous bone, either free or vascularized, the "gold standard" of bone grafting, may be efficient in these cases [4, 5].

Bone grafting with autotransplants is associated with causing further injury, expanding or creating a new surgical approach, considerably increasing the time of surgery, complication rate, and donor site morbidity. In addition, autogenous bone grafting using a microvascular technique can be performed only by highly skilled professionals in the setting of specialized medical institutions having equipment necessary not only to carry out such surgeries but also to control compatibility of vascular anastomoses and timely performance of revisualization procedures. At the same time, despite all difficulties, expended resources and funds, there is a high probability of thrombosis and vascular anastomosis failure causing loss of the autografts [6].

Even in case of strong indications for the autobone grafting, graft retention and its complete integration into a recipient site and the long-term outcome of the treatment are not always successful. Firstly, this is explained by a high degree of subsequent bioresorption of the grafted material (up to 40% and even more). Secondly, where the bone defect and/or the area of bone atrophy have an irregular shape, it is impossible to model the autograft (fibula, rib, scapula, cranial bones) precisely to the shape of the defect to be substituted so that the diastasis between the entire surface of the introduced material and the walls of the bone defect (bone recipient site) does not exceed 1 mm. This causes insufficient consolidation of the graft in the recipient bed area and also occurrence of post-surgical bone deformation, non-unions or excessive bioresorption of the autograft.

Thus, despite being the "gold standard" of bone substitute materials, bone autografts have a limited use, are not always efficient and are associated with a high frequency of complications. One of the key drawbacks of their use and one of the reasons of their insufficient efficiency is that they cannot be modeled precisely to the shape and size of the targeted bone defect. At the same time, a close contact of any bone substitute over the entire surface of the bone defect or the area of bone atrophy and complete immobilization are fundamental principles of the bone grafting [1]. When the autobone grafting is infeasible or turned out to be inefficient, medical practitioners have to use distraction osteogenesis, prosthetics or to reject the type of treatment that leads to the considerably lower quality of patients' life.

Therefore, it is highly pressing to develop new, more efficient bone substitutes that are able to replace or at least become an alternative in terms of efficiency to bone autografts including vascularized ones. According to the findings of the inventors' research, these problems may be solved by constructing a gene-activated porous biocompatible and biodegradable materials that exactly fit to the shape and size of the bone defects for substituting of which they were made using any available three-dimensional (3D) printing technology.

A variety of ordinary bone substitutes is known, such as allogenic and xenogenic bone matrixes from various processing technologies (demineralized, deproteinized, etc.), calcium phosphate ceramics, silicates, organic acids polymers as well as synthetic analogs or natural components of bone matrix organic and mineral substances. However, they all have only an osteoconductive action because no biologically active components are contained therein. Therefore, known bone substitutes are used only to substitute bone defects small in size (small volume), because they only have the capability to optimize reparative osteogenesis and are unable to provide its induction [7]. That type of products in the form of personalized blocks for repair of large bone defects are almost not used in clinical practice.

Another category includes activated bone substitutes that may be divided into groups of materials containing growth factors (proteins), living cells or gene constructions (nucleic acids).

Bone substitutes containing growth factors have a moderate osteoinductive action allowing activation of reparative osteogenesis. However, since growth factors have a short life span and short-distance action, and are known to quickly degrade under inflammatory conditions in the operative wound, the overall efficiency of these types of products appeared to be insufficient to substitute large bone defects. In this regard, there is only a limited number of studies that used three-dimensional printing technologies for constructing bone substitutes of a predetermined size and shape containing growth factors, and in all cases small size (about 1 cm$^3$) products were produced with far from optimal efficacy [8].

Examples of another, more efficient approach are associated with the development of personalized tissue-engineered bone grafts. Using various technologies for constructing scaffolds with a predetermined size and shape, researchers have manufactured personalized matrices that were combined with living cells. By this way, scaffolds of a predetermined size and shape acquire some osteogenic capacity and theoretically are able to provide a pronounced reparative osteogenesis induction. However, therapeutic potential of living cells forming a part of personalized bone grafts is limited by the oxygenation demand. In other words, many studies have proved a higher efficiency of such 3D-printed tissue-engineered bone grafts of small size (up to 1 cm$^3$) compared to the above mentioned known materials. However, in case of substitutions for large bone defects no effect has been achieved even with the ideal modeling of the scaffold shape and size to fit the defect geometry, because cells inevitably died without adequate blood supply.

There are known gene-activated bone substitutes containing or consisting of a scaffold and nucleic acids, i.e., a gene construction encoding a growth factor(s) [9].

A gene-activated bone substitute comprises a "scaffold-nucleic acid" complex which components were combined by various techniques, for example, chemical binding [7], using adjuvants (for example, gel biopolymer) [11], and immediate inclusion of a nucleic acid in a scaffold during its synthesis process.

Such products having an osteoinductive action are not limited by the oxygenation demand because no living cells were contained therein. However, many researchers think that the intensity of their osteoinductive action and, as a result, their efficiency when used to substitute bone defects is lower than that of the tissue-engineered bone grafts. The reason is a low transfection efficiency of the recipient site cells by gene constructs and also the use of "therapeutic strength" of one or two factors encoded by the gene constructs to induce the reparative process whereas cells of the tissue-engineered materials have a wider mechanism of action.

Due to the inefficiency and drawbacks of the abovementioned technical approaches, many research groups have taken the road of complicating their products by producing bone substitutes comprising complex carriers and combinations of biologically active components, e.g., gene constructions and cells, cells and growth factors, growth factors and gene constructions, and even growth factors, gene constructions and cells in a single item. However, production of such materials is excessively costly and their efficiency in substituting large bone defects remains insufficient.

Thus, there is a need in a personalized matrix that lacks deficiencies of known methods.

SUMMARY OF INVENTION

An object of the invention pertains to a personalized matrix of biocompatible and bioresorbable materials and their combination with a biologically active component such as gene constructions.

A method for manufacturing a personalized gene-activated implant for substituting a bone defect in a mammal is provided comprising: conducting computed tomography of an area of the bone defect in need of a bone grafting, modeling the bone defect or a bone grafting site based on data obtained in the computed tomography, thereby obtaining a model of the bone defect or bone grafting site, three-dimensional printing a biocompatible scaffold based on the model, thereby manufacturing the biocompatible scaffold for grafting and activating the biocompatible scaffold by at least one nucleic acid, thereby manufacturing the personalized gene-activated implant.

In one embodiment, during the manufacturing at least one element is incorporated into the biocompatible scaffold for subsequent fixation of the personalized gene-activated implant selected from the group consisting of a plate, miniplate, screw, miniscrew, pin, needle, rod and a combination thereof made of metals and/or bioresorbable materials.

Another object of the present invention is to provide a personalized gene-activated implant for substituting a bone defect in a mammal.

A method for treating a bone defect or bone tissue atrophy in a mammal is provided, comprising grafting a personalized gene-activated implant into a bone grafting site.

Another object of the present invention is to provide a method of constructing a personalized gene-activated material for substituting a bone defect in a mammal, comprising: determining a shape and a size of a bone defect or a bone atrophy area by at least one method selected from the group consisting of computed tomography, X-ray examination, and radiography, producing a personalized biocompatible scaffold having the determined shape and size from at least one bioresorbable material using a 3D-printing process, and combining the personalized biocompatible scaffold with a gene construction, thereby constructing the personalized gene-activated material.

In one embodiment, the 3D-printing process is at least one selected from the group consisting of stereolithography and photopolymerization.

In another embodiment, the gene construction is combined with the personalized biocompatible scaffold during or after the 3D-printing process.

In yet another embodiment, a material used for constructing the personalized biocompatible scaffold is at least one material selected from the group consisting of a calcium phosphate, hydroxyapatite, collagen, bioactive glass ceramic, and organic acid polymer.

In one embodiment, the personalized biocompatible scaffold is produced from a liquid material or a material temporally being in a liquid phase and the gene construction is combined with the material before or during the 3D-printing process.

In a different embodiment, the personalized biocompatible scaffold is produced from a solid material, which could be optionally granulated, and the gene construction is combined with the solid material in a liquid solution or as a part of a gel material before or during the 3D-printing process.

The personalized biocompatible scaffold may be combined with the gene construction after the 3D-printing process, wherein the gene construction is incubated at a predetermined temperature, exposure time, and mechanical impact with the personalized biocompatible scaffold, produced by the 3D-printing process.

In one embodiment, the liquid material is a gel, sol, or solution.

The 3D-printing may be conducted under sterile conditions.

In one embodiment, the gene construction is combined with the personalized biocompatible scaffold after it has been produced by the 3D-printing and the 3D-printing process is conducted under ambient conditions with subsequent sterilization of the personalized biocompatible scaffold.

In another embodiment, a bone defect is at least 1 cm$^3$.

In yet another embodiment, the at least one material may be combined with the gene construction before the 3D-printing.

The details of one or more embodiments of the invention are set forth in the accompanying description below. Although any methods and materials similar or equivalent to those described herein can be used in the practice or testing of the exemplified embodiments, the preferred methods and materials are now described. Other features, objects, and advantages of the exemplified embodiments will be apparent from the description and from the claims. In the specification and the appended claims, the singular forms include plural referents unless the context clearly dictates otherwise. The examples of embodiments are for illustration purposes only.

BRIEF DESCRIPTION OF DRAWINGS

The patent or application file contains at least one drawing executed in color. Copies of this patent or patent application publication with color drawing(s) will be provided by the office upon request and payment of the necessary fee.

A more complete appreciation of the embodiments and many of the attendant advantages thereof will be readily obtained as the same becomes better understood by reference to the following detailed description when considered in connection with the accompanying drawings, wherein:

FIGS. 1A and 1B schematically show a personalized gene-activated material suitable for substituting a cranial bone defect in a rabbit: 1A—top view; 1B—cross-sectional view through the center in the frontal plane.

FIG. 2 shows a constructed personalized gene-activated material suitable for substituting a cranial bone defect in a rabbit.

DETAILED DESCRIPTION OF THE EMBODIMENTS

Figure 3A:
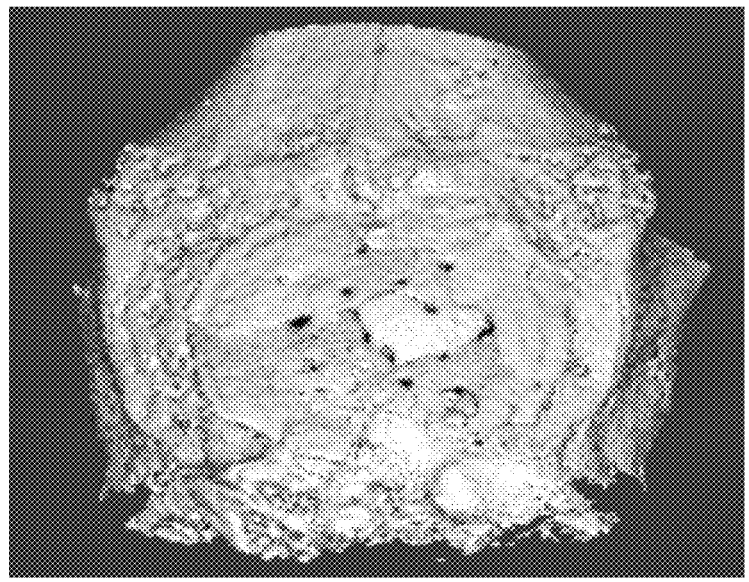
FIGS. 3A and 3B show a personalized gene-activated material substituted a bone defect; 6.5 months after implantation: 1—implant; 2—newly formed bone tissue; 3A—computed tomography; 3D reconstruction; 3B—histological image (staining: hematoxylin, eosin).

All publications, patent applications, patents, and other references mentioned herein are incorporated by reference herein in their entirety. Further, the materials, methods, and examples are illustrative only and are not intended to be limiting, unless otherwise specified.

The above mentioned materials, both ordinary and activated, comprising either growth factors or cells or gene constructs cannot be efficient for the repair of large bone defects due to the abovementioned aspects of the products' mechanism of action and unpredictable efficiency in substituting small and moderate in size defects.

However, despite the common opinion and trends (directed to producing more complicated and multicomponent bone substitutes) in the development, the present inventors have taken a different way of combining surgical and biomedical approaches in order to achieve advantageous results.

An object of the present invention is to provide a product and a process for its manufacturing and constructing a personalized matrix of biocompatible and bioresorbable materials and combining it with a biologically active component such as gene constructions. One aspect of the present invention distinguishing it from the known aspects (e.g., [9]) is the use of a 3D-printing process to produce a personalized product exactly fitting to the shape and size to the recipient site, i.e., the area of a bone defect or bone atrophy. In other words, the inventive product is produced in the way that after implantation into the recipient area, the diastasis between the material and congruent bone walls does not exceed 1 mm. A 3D-printing process is used to achieve personalized parameters and precise correspondence of the size and shape. An additional product component may be a fixing structure (e.g., reconstruction plates, screws, miniplates, miniscrews, wires, pins) incorporated into the material at some stage of manufacturing the implant. The presence of this component is needed if a bioresorbable material with insufficient mechanical characteristics was chosen as a scaffold for a gene construction that prevente reliable fixation in the recipient site with any standard techniques (e.g., metal constructions).

In one embodiment, a process for constructing of personalized gene-activated materials includes the following stages the order of which may vary:

1. Determining the exact shape and size of a bone defect or bone atrophy area. Standard radiological methods such as computed tomography, X-ray examination, radiography, and other methods may be used to this end.

2. Producing a personalized scaffold of a predetermined shape and size from bioresorbable materials using a 3D-printing process including stereolithography and/or photopolymerization.

3. Combining the scaffold with a gene construction at any stage of the production of the personalized scaffold or after its production.

A first stage is directed to planning morphometric parameters of the product to be manufactured and requires the same research methods as those used usually in the planning of surgical intervention. The most preferred option is computed tomography, an essential part of skeletal bones pathology diagnosis providing data for planning bone reparation procedures. Information obtained in the course of computed tomography may be used to model the shape and size of the bone defect and, accordingly, the shape and size of a personalized gene-activated implant using specially configured software (for example, "3D Slicer" available from NHI, USA).

Based on the obtained morphometric information, a master file could be formed for a 3D-printer or any other apparatus able to produce a three-dimensional implant with the predetermined parameters from the required bioresorbable materials. Considering the morphological and functional organization and regeneration of the bone tissue, preferred materials for constructing a scaffold may comprise calcium phosphates (e.g., β-tricalcium phosphates, octacalcium phosphates), hydroxyapatite, collagen, bioactive glass ceramics, organic acids polymers and other materials including combinations thereof. The bioresorbable materials selected for construction of personalized gene-activated implants may have any aggregative state and physical properties only influencing the choice of a particular 3D-printing process.

3D-printing of a scaffold may be accomplished by, for example, two fundamentally different methods. The first one includes direct printing of a scaffold from selected materials. The second one involves printing shaping elements, guides (from suitable materials) followed by their use as molds for "casting" (synthesis) a scaffold of the predetermined shape and size.

In the majority of cases, a 3D-printed scaffold has to be porous. The ideal porosity, geometry, size and localization of pores (micro- and macropores) correspond with the bone matrix morphology. However, the pattern of the empty spaces in a 3D-printed scaffold may significantly differ from the bone matrix structure, because of characteristics of the materials selected for production of the scaffold. In other words, if the material is mechanically strong and/or has a low biodegradation rate, the size and total amount of pores should be increased exceeding the porosity of the native bone matrix. Generally, a range of the size of macropores of a 3D-printed scaffold is 100-2000 μm, micropores—5-20 μm, porosity—40-90%.

For the production of a personalized gene-activated material, a scaffold and gene constructions (for example, plasmid DNA) are combined. This part of the process can also be implemented by a number of methods partly definable by the nature of bioresorbable materials selected for the production of the scaffold. If the scaffold is produced from a liquid or liquid-like material (e.g., gel, sol, solution) or a material temporally being in a liquid phase, a gene construction may be introduced therein before or during the 3D-printing. If a solid material (for example, granulated) is used, gene constructions may be added to a liquid solution or as a part of a gel material containing them before or during the 3D-printing. In one embodiment, a produced personalized scaffold is combined with a gene construction after the 3D-printing. To this end, the gene construction at various concentrations in the form of a solution or as a part of a gel may be incubated under different conditions (temperature, exposure time, mechanical impact) with the "printed" scaffold.

If a gene construction is combined with a scaffold before or during its 3D-printing, it is preferred to carry out the 3D-printing under sterile conditions, i.e., in class A or B clean rooms. However, if the gene construction is combined with the scaffold after it has been produced, 3D-printing could be performed in the room of any class with subsequent sterilization of the resulting personalized scaffold and combining with a gene construction under sterile conditions thereafter.

Nucleic acids (biologically active gene constructions, DNA or RNA) include or consist of a therapeutic gene and its intracellular delivery system (vector). Vectors are divided into two main groups, viral and non-viral. In the first case, a transgene is incorporated into a particle of retro-, lenti-, and adenovirus or adeno-associated virus, and, in the second case, a transgene is incorporated into a plasmid, a circular molecule of a nucleic acid containing several additional sequences providing transgene expression. Viral and non-viral delivery systems differ in their efficacy of transfection. 40% or more of viral gene constructions can enter target cells, and the rate of plasmid DNA uptake ("naked DNA") does not exceed 1-2% due to its size and negative charge. Some approaches have been proposed (physical and chemical) to increase the efficacy of plasmid DNA transfection up to 8-10% range, for example, binding with cationic polymers. A list of the most preferred therapeutic genes includes, but is not limited by those encoding a vascular endothelial growth factor (VEGF), stromal-derived factor-1 (SDF-1), bone morphogenetic proteins (BMP), and insulin-like growth factor-1 (IGF-1).

The amount of nucleic acids in a personalized gene-activated implant has to be sufficient to provide the bone tissue repair. As for non-viral gene constructions, a range of concentrations of 50-500 μg, and all intermediate concentrations, per 1 g of the scaffold allows achieving the complete bone regeneration. However, higher concentrations could be used, for instance exceeding 1 mg per 1 g of scaffold, because even high doses of plasmid DNA have been shown to be safe. As for viral gene constructions, the amount of viral particles carrying nucleic acids is at least $1 \times 10^{10}$ per 1 mg of the scaffold. The upper limits in both variants of gene constructions could be increased depending on scaffold materials and the size of the defect to be replaced.

It has been surprisingly found in the research partly described in the examples herebelow that optimal results could be achieved using personalized gene-activated materials produced by a 3D-printing process even in case of the repair of large bone defects. In other words, it is precisely the congruence and tight adherence of the gene-activated material to all surfaces of a recipient site that enables its efficiency. At the same time, the identical personalized scaffold but without gene constructions was completely inefficient and the non-personalized gene-activated implant made of the same materials and having a standard size and shape was not efficient enough.

The advantageous effects obtained by the present inventors are likely to be explained by the fact that once implanted into the area of a large bone defect, gene constructions of the standardly-shaped and sized non-personalized gene-activated material do not directly contact the recipient bed cells and fail to reach the target cells. Moreover, diastasis of more than 1 mm between bone walls and the gene-activated material provides for most released gene constructions to be destroyed and quickly eliminated by blood clot enzymes and the inflammatory liquid feeling this space. At the same time, the migration of resident cells into the implant is not active enough due to significant space between the product surface and bone defect walls. As a result, considering the low transfection efficiency, especially in case of plasmid DNA, nucleic acids do not enter the cells in quantities sufficient to enable a therapeutic effect.

In contrast, the inventive personalized gene-activated materials adhere tightly to all surfaces of the recipient bed with a "free space" being less than 1 mm in length. This facilitates faster and more massive migration of cells into the product structure and shortens the distance that has to be covered by gene constructions on the way to the target cells. Due to the lack of space between the gene-activated material and bone defect walls, the shortening of the distance provides preservation of more gene constructions, which is extremely important for achieving a therapeutic effect.

Therefore, full compliance between the product's shape and size and the recipient bed's parameters precisely in case of gene-activated materials is important for achieving a therapeutic effect of the product. Finding out this fact has allowed the inventors to develop a bone substitute efficient for the repair of large bone defects (at least 1 cm$^3$ or more than 1 cm$^3$). However, detailed mechanisms of the discovered efficiency of precisely personalized gene-activated materials need further research and elaboration.

Having solved in part the problem of large bone defects substitutions in the aspect of biomedical methods, the inventors have faced another problem, a surgical one. The problem is that a gene-activated material to implement its osteoinductive action has not only to adhere tightly to all recipient bed surfaces immediately after the implantation but also to remain in such position all the time until complete integration with the surrounding bone tissue. In other words, a personalized bone graft has to be securely fixed in the recipient site otherwise it may shift and spaces could form between the implant and recipient area that could impair the biological action, give rise to motility and even fall-out. This problem has been solved by the investors in cases where the scaffold contains a mechanically strong material allowing standard fixation (screws, miniscrews, microscrews, pins, needles)—any fixtures could be screwed or inserted therein directly during surgery without destroying the implant. However, scaffold materials are often fragile and are not sufficiently strong. For example, porous scaffolds of calcium phosphates break easily at the attempt to drill for fixation. It is extremely difficult or even impossible to fix such materials directly during surgery.

The inventors have developed additional process stages and variants of the personalized gene-activated materials made of scaffolds that do not have mechanical strength. A solution is to place fixation elements into the personalized gene-activated bone graft during scaffold manufacturing. One way is to introduce a special core made of a metal or a strong bioresorbable material into the interior scaffold structure that may have holes for fixation elements (screws, mini screws, microscrews, pins, needles). Channels leading to the core (or holes in the core) should be formed at the surface of the implant where the product is supposed to be fixed. Another option is to place an external fixation system (for example, a miniplate with miniscrews) at the predetermined position and to produce a scaffold of the predetermined shape and size already with the fixation elements. As a result, a personalized gene-activated material may comprise either internal (core) or external fixtures.

In one embodiment, fixation elements are selected at the first stage of the personalized gene-activated implant production based on a surgical plan proposed by a medical practitioner. For this, a 3D-bone model may be initially manufactured having a specific defect area, atrophy or pathological site the correction of which would entail formation of a bone defect. This model has to be made available to a medical practitioner planning the surgery. A physician would reproduce the planned manipulations (e.g., resection of a bone fragment, grinding of the bone defect walls) and locate fixation elements (e.g., structures made of metals or strong bioresorbable materials) on the model for immobilizing bone fragments and the personalized gene-activated implant. The model with the fixation elements secured thereon at the correct position could be used to calculate morphometric parameters of the personalized gene-activated implant and its manufacturing.

Having generally described this invention, a further understanding can be obtained by reference to certain specific examples which are provided herein for purposes of illustration only, and are not intended to be limiting unless otherwise specified.

EXAMPLES

Example 1

Personalized Gene-Activated Material without "Embedded" Fixation Elements

Before manufacturing one of the variants of the personalized gene-activated material without fixtures by the method of one of the embodiments, an adequate biological model of the bone defect having critical dimensions was defined. The inventors were guided by the following criteria in the selection of a research model: 1) a bone defect had to be of maximum dimensions; and 2) allowed the block to be reliably fixed without using any metal constructions in the implantation area. Considering the above cited criteria, the inventors developed an experimental model of a defect of rabbit's cranial bones having a diameter of 20 mm. Cranial osteotomy was performed with a drill to form the bone defect without damaging the dura mater of the brain and preserving 1-mm wide fragments of the internal cortical plate protruding 1 mm towards the center of the defect at the 1, 5, 7, and 11 o'clock projections. The preservation of these bone fragments at said positions as support points in combination with the bone defect dimensions became a distinctive feature of the model. The model allowed a personalized gene-activated implant to be immobilized within the bone defect without using additional fixing techniques.

Multispiral computed tomography of the rabbit's cranium was performed before the surgery. Using 3D Slicer software (NHI, USA), the inventors performed a manual segmentation of the planned bone defect with the center located at the sagittal suture projection equidistantly from the frontoparietal and parietooccipital sutures. Considering the calculated morphometric parameters of the planned bone defect, 3D-printing of the octacalcium phosphate block was performed. The block was shaped as a convex disk of 1.3 mm in thickness, 20 mm in diameter and was provided with 17 perforations for cerebral decompression after the cranial bone substitution (FIG. 1, FIG. 2).

The scaffold produced by the 3D-printing was combined with a gene construction (plasmid DNA with a gene encoding a vascular endothelial growth factor (VEGF)) according to the predefined laboratory protocol based on chemically binding the nucleic acids to the scaffold's calcium:

1) washing the scaffold (incubation with 0.5 M phosphate buffer in a 5-ml volume at 37° C. with continuing agitation for 12 hours);

2) equilibration (treating with 10 mM phosphate buffer in a 5-ml volume at 37° C. with continuing agitation, 3 times for 10 min each time);

3) drying the scaffold (incubation at 37° C. until thorough drying for 3 hours).

4) applying the gene constructions (incubation with the plasmid DNA solution in 10 mM phosphate buffer at a concentration of 1 µg/µL at 37° C. with continuing agitation for 12 hours).

5) washing unbound plasmid DNA (treating with 5 mM phosphate solution a 5-ml volume 3 times) off the product;

6) drying (incubation at 37° C. until thorough drying for 3 hours).

Figure 3B:
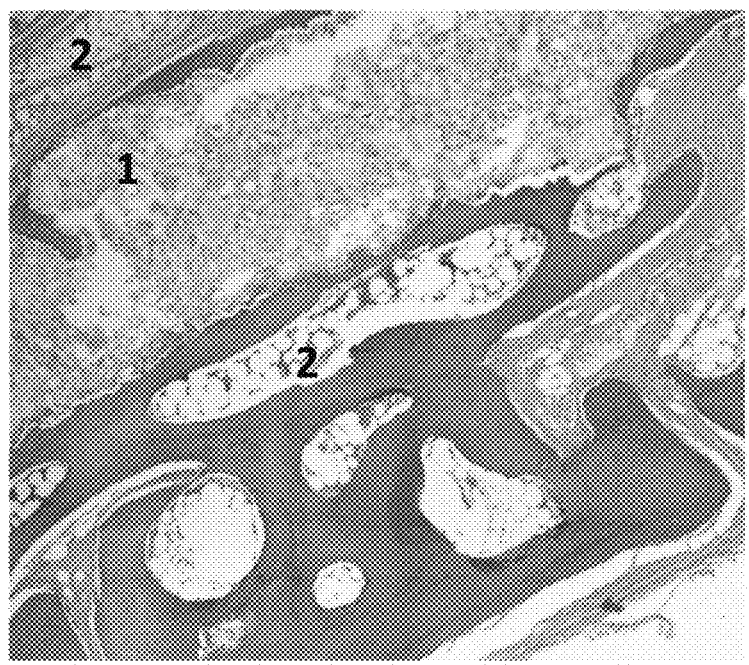

6.5 months after the bone grafting with the personalized gene-activated substitute (implant), the rabbit's cranial bone integrity was completely repaired. The implant did not resorb but its peripheral areas were completely integrated with the surrounding bone tissue. Moreover, a 3-6 mm long newly formed bone tissue was formed along the internal and external surfaces of the personalized gene-activated graft. According to the computed tomography and histological study, the newly formed bone tissue tightly adhered to the implant without forming any connective-tissue interlayer or capsule was detected (FIG. 3).

Figure 4:
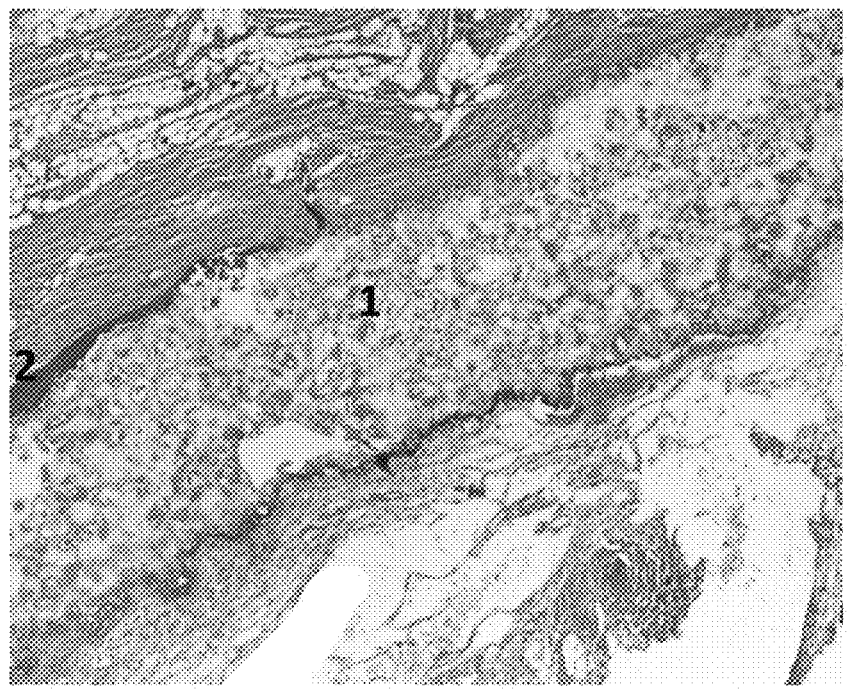
FIG. 4 shows a personalized material not activated by gene constructions that substituted a bone defect; 6.5 months after implantation: 1—implant, 2—newly formed bone tissue. Histological image (staining: hematoxylin, eosin).

In the absence of the gene-activated construction, the newly formed bone tissue volume was considerably less and the bone proceeding from the periphery did not exceed 1-2 mm (FIG. 4).

Example 2

Personalized Gene-Activated Material with "Embedded" Fixation Elements

In order to study this variant of the personalized gene-activated material, the inventors have developed another model: a 36-mm long defect of the rabbit's shin bones with stepwise-edged proximal and distal bone fragments.

Figure 5:
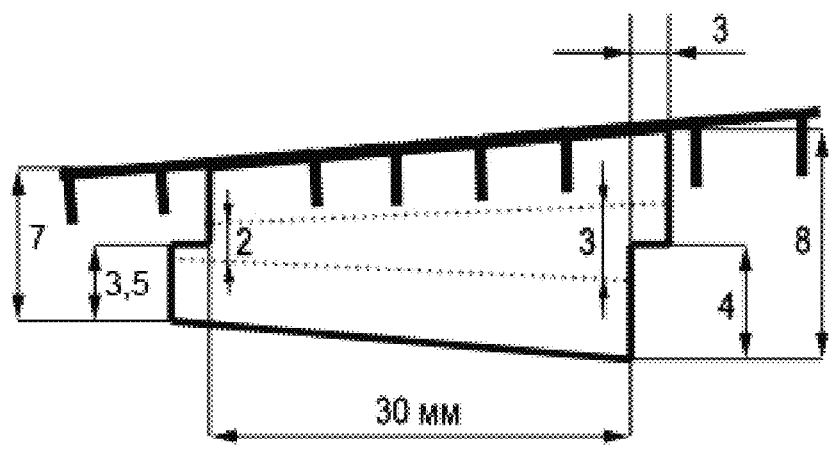
FIG. 5 schematically shows a personalized gene-activated material with locating elements, suitable for substituting a large defect of rabbit's shin bones.

A personalized gene-activated implant (FIG. 5) was created using a method of one of the embodiments.

Figure 6:
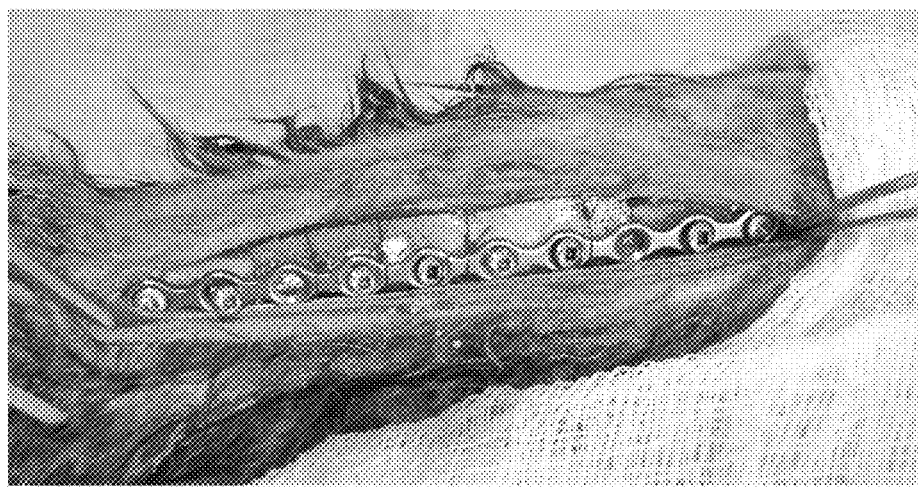
FIG. 6 shows a personalized gene-activated implant fixed in a bone defect with a miniplate and miniscrews.

At the first stage, 3D-printing was carried out to manufacture shaping elements wherein the miniplate and miniscrews intended for fixing the implant were positioned. Using the resulting mold, a scaffold was synthesized from tricalcium phosphate exactly fitting to the mold parameters and containing fixation elements. The implant was combined with the gene construction (plasmid DNA with vegf and sdf genes (encoding a stromal cell growth factor)) according to the abovementioned protocol. The resulting personalized gene-activated substitute with the "embedded" fixation system was implanted into the rabbit's shin bones defect exactly fitting the implant parameters (FIG. 6).

Figure 7:
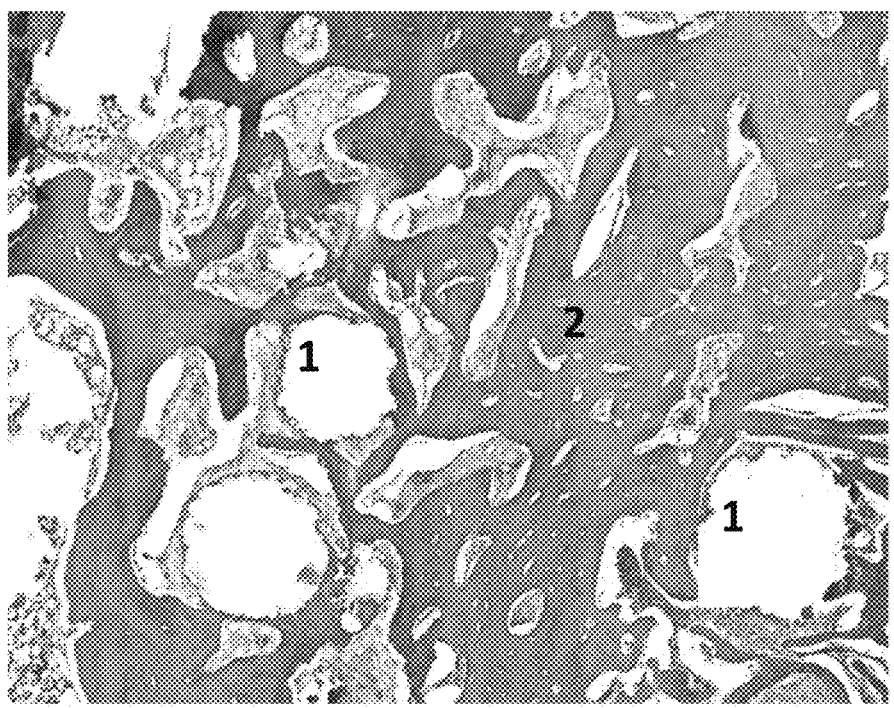
FIG. 7 shows a personalized gene-activated material with locating elements that substituted a bone defect; 3 months after implantation: 1—implant, 2—newly formed bone tissue. Histological image (staining: hematoxylin, eosin).

3 months later, the support ability of the extremity was completely restored. The implant did not resorb by the end of this time and its peripheral areas were completely integrated with bone fragments (FIG. 7).

The developed method for constructing a personalized gene-activated material and variants thereof made it possible to manufacture medical products efficient for substitution of bone defects including large in size bode defects.

LIST OF THE CITED REFERENCES

1. Kulakov L. A., Robustova T. G., Nerobeev L. I., editors. Dental Surgery and Maxillofacial Surgery. National guidance. Moscow, GEOTAR-Media, 2010; 928 p.;
2. Pipitone P S, Rehman S. Management of traumatic bone loss in the lower extremity. Orthop Clin North Am. 2014 October; 45(4):469-82;
3. Tevlin R, McArdle A, Atashroo D, Walmsley G G, Senarath-Yapa K, Zielins E R, Paik K J, Longaker M T, Wan D C. Biomaterials for craniofacial bone engineering. J Dent Res. 2014 December; 93(12):1187-95;
4. Al-Nawas B, Schiegnitz E. Augmentation procedures using bone substitute materials or autogenous bone—a systematic review and meta-analysis. Eur J Oral Implantol. 2014 Summer; 7 Suppl 2:S219-34;
5. Nkenke E, Neukam F W. Autogenous bone harvesting and grafting in advanced jaw resorption: morbidity, resorption and implant survival. Eur J Oral Implantol. 2014 Summer; 7 Suppl 2:S203-17;
6. Han Z, Li J, Li H, Su M, Qin L. Single versus dual venous anastomoses of the free fibula osteocutaneous flap in mandibular reconstruction: A retrospective study. Microsurgery. 2013 Sep. 3. doi: 10.1002/micr.22176. [Epub ahead of print];
7. Deev R. V., Drobyshev A. Yu., Bozo I. Ya. et al. Construction and biological effect evaluation of gene-activated osteoplastic material with human VEGF gene. Cellular Transplantation and Tissue Engineering, 2013; VIII (3): 78-85;
8. Strobel L A, Rath S N, Maier A K et al. Induction of bone formation in biphasic calcium phosphate scaffolds by bone morphogenetic protein-2 and primary osteoblasts. J Tissue Eng Regen Med. 2014 March; 8(3):176-85;
9. Goldstein S. A. In vivo gene transfer methods for wound healing, U.S. Pat. No. 2,170,104, Oct. 7, 2001;
10. Wegman F., Bijenhof A., Schuijff L. et al. Osteogenic differentiation as a result of BMP-2 plasmid DNA based gene therapy in vitro and in vivo. Eur. Cell Mater. 2011; 21: 230-42.

The invention claimed is:

1. A method for manufacturing a personalized gene-activated implant for regeneration of bone tissue of a bone defect in a mammal, the method comprising:
    conducting computed tomography of an area of the bone defect in need of a bone grafting, wherein the bone defect is at least 1 cm$^3$,
    modeling the bone defect or a bone grafting site based on data obtained in the computed tomography, thereby obtaining a model of the bone defect or bone grafting site,
    three-dimensional printing by a direct three-dimensional printing from a material comprising calcium phosphate a biocompatible scaffold comprising micropores, macropores, or a combination hereof corresponding to dimensions of the model, thereby manufacturing the biocompatible scaffold for grafting and activating the biocompatible scaffold by at least one nucleic acid, or
    three-dimensional printing by a direct three-dimensional printing from a material comprising calcium phosphate a biocompatible scaffold comprising micropores, macropores, or a combination hereof corresponding to dimensions of the model, and simultaneously with the printing, activating the biocompatible scaffold by at least one nucleic acid,
    thereby manufacturing the personalized gene-activated implant that has a shape so that to adhere to all walls and surfaces of the bone defect or bone grafting site in the mammal with a distance between the implant and the walls and surfaces of the bone defect or bone grafting site of not more than 1 mm,
    wherein during the manufacturing at least one element is incorporated into the biocompatible scaffold for subsequent fixation of the personalized gene-activated implant,
    wherein the at least one nucleic acid of the activated biocompatible scaffold is located on a surface of the biocompatible scaffold,
    wherein the at least one nucleic acid is plasmid DNA comprising a gene encoding at least one protein selected from the group consisting of a vascular endothelial growth factor (VEGF), stromal-derived factor-1 (SDF-1), bone morphogenetic proteins (BMP), and insulin-like growth factor-1 (IGF-1), and
    wherein a concentration of the at least nucleic acid is from 50 µg to 500 µg per 1 g of the biocompatible scaffold.

2. The method according to claim 1, wherein the at least one element incorporated into the biocompatible scaffold for subsequent fixation is at least one selected from the group consisting of a plate, miniplate, screw, miniscrew, pin, needle, rod and a combination thereof made of metals and bioresorbable materials.

3. A personalized gene-activated implant for regeneration of bone tissue of a bone defect in a mammal, the implant comprising a biocompatible scaffold comprising calcium phosphate and is activated by at least one nucleic acid located on a surface of the biocompatible scaffold, wherein the biocompatible scaffold comprises micropores, macropores, or a combination hereof,
    wherein the implant is manufactured by the method, comprising:

conducting computed tomography of an area of the bone defect in need of a bone grafting, wherein the bone defect is at least 1 cm$^3$, modeling the bone defect or a bone grafting site based on data obtained in the computed tomography, thereby obtaining a model of the bone defect or bone grafting site, and three-dimensional printing by a direct three-dimensional printing from a material comprising calcium phosphate a biocompatible scaffold corresponding to dimensions of the model, thereby manufacturing the biocompatible scaffold for grafting, and further activating the printed biocompatible scaffold by at least one nucleic acid, or three-dimensional printing by a direct three-dimensional printing from a material comprising calcium phosphate a biocompatible scaffold corresponding to dimensions of the model and simultaneously with the printing, activating the biocompatible scaffold by at least one nucleic acid, thereby manufacturing the personalized gene-activated implant that has a shape so that to adhere to all walls and surfaces of the bone defect or bone grafting site in the mammal with a distance between the implant and the walls and surfaces of the bone defect or bone grafting site of not more than 1 mm, wherein during the manufacturing at least one element is incorporated into the biocompatible scaffold for subsequent fixation of the personalized gene-activated implant, wherein the at least one nucleic acid is plasmid DNA comprising a gene encoding at least one protein selected from the group consisting of a vascular endothelial growth factor (VEGF), stromal-derived factor-1 (SDF-1), bone morphogenetic proteins (BMP), and insulin-like growth factor-1 (IGF-1), and wherein a concentration of the at least nucleic acid is from 50 μg to 500 μg per 1 g of the biocompatible scaffold.

4. A method for treating a bone defect or bone tissue atrophy in a mammal, comprising grafting the personalized gene-activated implant of claim 3 into a bone grafting site.

5. The personalized gene-activated implant of claim 3, wherein the at least one element incorporated into the biocompatible scaffold for subsequent fixation is at least one selected from the group consisting of a plate, miniplate, screw, miniscrew, pin, needle, rod and a combination thereof made of metals and bioresorbable materials.

6. The method of claim 1, wherein a size of the macropores of the three-dimensionally printed biocompatible scaffold is from 100 μm to 2000 μm.

7. The personalized gene-activated implant of claim 3, wherein a size of the macropores of the three-dimensionally printed biocompatible scaffold is from 100 μm to 2000 μm.

8. The method of claim 1, wherein a porosity of the three-dimensionally printed biocompatible scaffold is from 40 to 90%.

9. The personalized gene-activated implant of claim 3, wherein a porosity of the three-dimensionally printed biocompatible scaffold is from 40 to 90%.

10. The method of claim 1, wherein the at least one nucleic acid comprises a gene encoding a vascular endothelial growth factor (VEGF).

11. The personalized gene-activated implant of claim 3, wherein the at least one nucleic acid comprises a gene encoding a vascular endothelial growth factor (VEGF).

12. The method according to claim 1, wherein the at least one element for fixation of the personalized gene-activated implant is an internal core or an external fixation element, wherein the internal core comprises a metal or a strong bioresorbable material, the method further comprises: incorporating during the manufacturing of the biocompatible scaffold the internal core into an interior of a structure of the biocompatible scaffold such that at least one hole for at least one fixation element selected from the group consisting of a screw, miniscrew, microscrew, pin, rod, and needle is made and channels leading to the core or the at least one hole in the core are formed at the surface of the personalized gene-activated implant where the implant is to be fixed, or placing the external fixation element comprising a miniplate comprising miniscrews at a predetermined position during the manufacturing.

13. The method according to claim 12, wherein the personalized gene-activated implant comprises the internal core.

14. The method according to claim 12, wherein the personalized gene-activated implant comprises the external fixture element.

15. A method for manufacturing a personalized gene-activated implant for regeneration of bone tissue of a bone defect in a mammal, the method consisting of:

conducting computed tomography of an area of the bone defect in need of a bone grafting, wherein the bone defect is at least 1 cm$^3$, modeling the bone defect or a bone grafting site based on data obtained in the computed tomography, thereby obtaining a model of the bone defect or bone grafting site, three-dimensional printing by a direct three-dimensional printing from a calcium phosphate martial a biocompatible scaffold comprising micropores, macropores, or a combination thereof corresponding to dimensions of the model, thereby manufacturing the biocompatible scaffold for grafting and activating the biocompatible scaffold by at least one nucleic acid, or three-dimensional printing by a direct three-dimensional printing from a calcium phosphate material a biocompatible scaffold comprising micropores, macropores, or a combination thereof corresponding to dimensions of the model, and simultaneously with the printing, activating the biocompatible scaffold by at least one nucleic acid, thereby manufacturing the personalized gene-activated implant that has a shape so that to adhere to all walls and surfaces of the bone defect or bone grafting site in the mammal with a distance between the implant and the walls and surfaces of the bone defect or bone grafting site of not more than 1 mm, wherein the at least one nucleic acid of the activated biocompatible scaffold is located on a surface of the biocompatible scaffold, wherein the at least one nucleic acid is plasmid DNA comprising a gene encoding at least one protein selected from the group consisting of a vascular endothelial growth factor (VEGF), stromal-derived factor-1 (SDF-1), bone morphogenetic proteins (BMP), and insulin-like growth factor-1 (IGF-1), and wherein a concentration of the at least nucleic acid is from 50 μg to 500 μg per 1 g of the biocompatible scaffold.

16. The method of claim 1, wherein a size of the micropores of the three-dimensionally printed biocompatible scaffold is from 5 μm to 20 μm.

17. The personalized gene-activated implant of claim 3, wherein a size of the micropores of the three-dimensionally printed biocompatible scaffold is from 5 μm to 20 μm.

18. The personalized gene-activated implant of claim 15, wherein a size of the macropores of the three-dimensionally printed biocompatible scaffold is from 100 μm to 2,000 μm.

19. The personalized gene-activated implant of claim 3, wherein a size of the micropores of the three-dimensionally printed biocompatible scaffold is from 5 μm to 20 μm.

\* \* \* \* \*